United States Patent [19]

Falk

[11] 4,102,916
[45] Jul. 25, 1978

[54] PERFLUOROALKYLTHIOAMINIMIDE DERIVATIVES

[75] Inventor: Robert A. Falk, New City, N.Y.

[73] Assignee: Ciba-Geigy Corporation, Ardsley, N.Y.

[21] Appl. No.: 747,112

[22] Filed: Dec. 2, 1976

[51] Int. Cl.$^2$ ............... C07C 143/155; C07C 143/08
[52] U.S. Cl. ..................... 260/501.12; 260/458 C; 260/459 A; 260/459 R; 260/561 S; 260/561 A; 260/561 HL; 260/458 F
[58] Field of Search ........ 260/561 S, 561 A, 561 HL, 260/501.12, 458 F, 458 C, 459 A, 459 C

[56] References Cited

U.S. PATENT DOCUMENTS

| | | | |
|---|---|---|---|
| 3,172,910 | 3/1965 | Brace | 260/561 S |
| 3,766,274 | 10/1973 | Anello | 260/561 HL |
| 3,940,435 | 2/1976 | Hiestand | 260/481 R |
| 3,963,776 | 6/1976 | Middleton | 260/561 H |

*Primary Examiner*—Arthur P. Demers
*Attorney, Agent, or Firm*—Edward McC. Roberts; Michael W. Glynn; Prabodh I. Almaula

[57] ABSTRACT

The perfluoroalkyl compounds containing aminimide groups have the formula

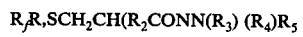

wherein $R_f$ is a perfluoroalkyl, $R_1$ is alkylene, oxy or thioalkylene, or alkyleneiminoalkylene; $R_2$ is hydrogen or alkyl; $R_3$ and $R_4$ are alkyl or together with the nitrogen form a heterocyclic ring and $R_5$ is alkyl which may contain hydroxyl or carboxyl groups or an anionic function such as sulfonate, sulfate or carboxylate, are prepared by the addition of a perfluoroalkylthiol to an aminimide of an α, β-unsaturated acid. These compounds are useful as surfactants.

8 Claims, No Drawings

PERFLUOROALKYLTHIOAMINIMIDE DERIVATIVES

DETAILED DISCLOSURE

The novel perfluoroalkylthioaminimide compounds of this invention are the formula $$R_fR_1SCH_2CHR_2CONNR_3R_4R_5$$

wherein $R_f$ is straight or branched chain perfluoroalkyl of 1 to 18 carbon atoms or said perfluoroalkyl substituted by perfluoroalkoxy of 2 to 6 atoms;

$R_1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms;

$R_2$ is hydrogen or straight or branched chain alkyl of 1 to 6 carbon atoms;

$R_3$ and $R_4$ each is independently straight or branched chain alkyl of 1 to 22 carbon atoms or $R_3$ and $R_4$ are each alkylene of 2 or 3 carbons which, together with the nitrogen to which they are boned and optionally additional oxygen or nitrogen, form a heterocyclic ring and $R_5$ is straight or branched chain alkyl of 1 to 22 carbon atoms that may also contain 1 to 2 hydroxyl groups, a free carboxylic acid group, or an anionic function selected from sulfonate, sulfate, or carboxylate.

Particularly useful compounds are those where $R_f$ is straight or branched chain perfluoroalkyl of 6 to 12 carbon atoms or said perfluoroalkyl substituted by perfluoroalkoxy of 2 to 6 atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen or methyl as a third substituent;

$R_2$ is hydrogen or methyl;

$R_3$ and $R_4$ each is independently straight chain alkyl of 1 to 12 carbon atoms; $R_3$ and $R_4$ combined can also represent a biradical which together with the nitrogen or other hereto atom forms a heterocyclic ring; and $R_5$ is straight chain alkyl of 1 to 3 carbon atoms that may also contain 1 hydroxyl group, a free carboxylic acid group, an anionic function including sulfonate, sulfate, or carboxylate, or oxygen.

The novel $R_f$-surfactants described herein can be obtained either:

(a) directly by the base-catalyzed addition of a perfluoroalkylthio of formula $$R_fR_1SH$$

to an α, β-unsaturated aminimide of formula $CH_2=CR_2CON^-N^+R_4R_5$ where $R_f$ is straight or branched chain perfluoroalkyl of 1 to 18 carbon atoms or said perfluoroalkyl substituted by perfluoroalkoxy of 2 to 6 atoms.

$R_1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms.

$R_2$ is hydrogen or straight or branched chain alkyl of 1 to 6 carbon atoms.

$R_3$ and $R_4$ each is independently straight or branched chain alkyl of 1 to 22 carbon atoms; $R_3$ and $R_4$ combined can also represent a biradical which together with the nitrogen or other hetero atom forms a heterocyclic ring.

$R_5$ is straight or branched chain alkyl of 1 to 22 carbon atoms that may also contain 1 to 2 hydroxyl groups, a free carboxylic acid group, an anionic function including sulfonate, sulfate, or carboxylate.

(b) indirectly by the further reaction of the above products with such alkylation reagents as chloroacetic acid, sodium chloroacetate, propane sultone, propiolactone and the like, to yield other amphoteric and the like, to yield other amphoteric surfactants.

One group of preferred compounds has the formula $$R_fCH_2CH_2SCH_2CHCH_3CON^-N^+(CH_3)_2CH_2CHOHCH_3$$

and $$R_fCH_2CH_2SCH_2CHCH_3CON^-N^+(CH_3)_3$$

where $R_f$ is perfluoroalkyl of 6 to 12 carbon atoms or where $R_f$ is perfluoroalkoxyperfluoroalkyl of 4 to 12 atoms, and especially where $R_f$ is $(CF_3)_2CFO(CF_2CF_2)y-$ where $y$ is an integer from 1 to 6.

In one embodiment, the α,β-unsaturated amide has the formula $$CH_2=CCH_3CON^-N^+(CH_3)_2R_6$$

where $R_6$ is a methyl, or 2-hydroxypropyl group

Such compounds are disclosed in the following patents: U.S. Pat. No. 3,527,802 and U.S. Pat. No. 3,485,806.

Perfluoroalkyl thiols useful herein are well documented in the prior art. For example, thiols of the formula $R_fR'$—SH have been described in a number of U.S. Pat. Nos. including 2,894,991; 2,961,470; 2,965,677; 3,088,849; 3,172,190; 3,544,663; and 3,655,732.

U.S. Pat. No. 3,655,732 discloses mercaptans of formula $$R_f-R'-SH$$

where R' is alkylene of 1 to 16 carbon atoms and $R_f$ is perfluoroalkyl and teaches that halides of formula $R_fI$—R'— hal are well known; reaction of $R_fI$ with ethylene under free-radical conditions gives $R_f(CH_2CH_2)_aI$ as is further taught in U.S. Pat. Nos. 3,088,849; 3,145,222; 2,965,659 and 2,972,638.

U. S. Pat. No. 3,655,732 further discloses compounds for formula $R_f$—R'—X—R"—SH
where R' and R" are alkylene of 1 to 16 carbon atoms, with the sum of the carbon atoms of R' and R" being no greater than 25; $R_f$ is perfluoroalkyl of 4 through 14 carbon atoms and X is —S—or—NR''' is hydrogen or alkyl of 1 through 4 carbon atoms.

U.S. Pat. No. 3,544,663 teaches that the mercaptan $$R_fCH_2CH_2SH$$

where $R_f$ is perfluoroalkyl of 5 to 13 carbon atoms, can be prepared by reacting the perfluoroalkyl alkylene iodide with thiourea or by adding $H_2S$ to a perfluoroalkylsubstituted ethylene ($R_f$—CH=CH$_2$), which in turn can be prepared by dehydrohalogenation of the halide $R_f$—$CH_2CH_2$—hal.

The reaction of the iodide $R_f$—R'—I with thiourea followed by hydrolysis to obtain the mercaptan $R_f$—R—'—SH is the preferred synthetic route. The reaction is applicable to both linear and branched chain iodides. Many useful perfluoroalkoxyalkyl iodides are described in Australian application No. 336,968 filed Apr. 24, 1968, of general formula $$(CF_3)_2CHOCF_2CF_2(CH_2CH_2)m^1$$

where $m$ is 1–3.

Particularly preferred herein are the thiols of formula $$R_fCH_2CH_2SH$$

where
$R_f$ is perfluoroalkyl of 6 to 12 carbon atoms.
These $R_f$-thiols can be prepared from $R_fCH_2CH_2I$ and thiourea in very high yield.

Alkylation of aminiimide type adducts is less well-known, but has been reported; Chem. Reviews 73 (3) 255-91 (1973). It yields N or O alkylated compounds, as shown below

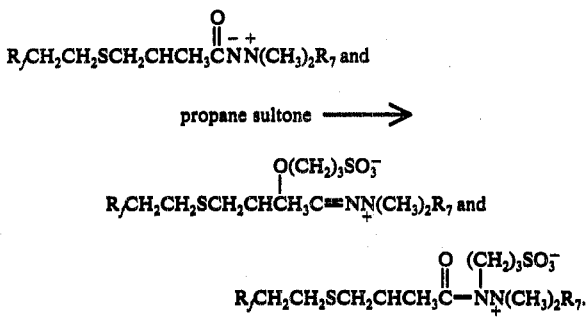

The addition of a perfluoroalkylthiol of formula $R_fR_1SH$ to an $\alpha,\beta$-unsaturated aminimide proceeds poorly by base catalysis and it is necessary to use an azotype free-radical catalyst.

The reaction temperature and choice of azo-type free-radical catalyst are considered to be mutually dependent. The temperature range of 40° to 100° C is one wherein the formation of undesirable by-products is minimized and wherein the reaction products are stable. In order to achieve a reasonable reaction rate of these temperatures, it is desirable to use an azo-type catalyst that is reactive to a reasonable extent in this temperature range. It is, therefore, preferred to use an azo-type free-radical catalyst having a 1-hour half-life temperature of 40° to about 100° C.

Suitable solvents are such in which the reactants are soluble at reaction temperatures and include aliphatic or aromatic hydrocarbons such as heptane, benzene, toluene, etc; chlorinated for fluorinated aliphatic or aromatic hydrocarbons such as methylene chloride, chloroform, methyl chloroform, carbon tetrachloride, trichloroethylene, perchloroethylene, Freon's such as 1,1,2-trifluoro-1.2.2-trichloroethane, etc., chlorobenzene, benzotrifluoride or hexafluoroxylene, ketones, esters and ethers such as acetone, methyl isobutyl ketone, ethyl acetate and higher homologs, dialkyl ethers, tetrahydrofuran, ethylene glycol monomethyl or monoethyl ether, ethylene glycol dimethyl or diethyl ether, and acetonitrile.

If possible it is preferred to carry out the addition reaction in bulk.

Perfluoroimides are described in the prior art, U.S. Pat. No. 3,488,389 having the general formula: $R_fCON^-N^+R_1R_2R_3$.

The synthesis fo these aminimides is contingent upon the availability of $R_fCOOH$, whereas the aminimides of the present invention are not.

The novel fluorochemical surfactants of this invention are useful to improve or impart properties such as: wetting, penetration, spreading, leveling, foam stability, flow properties, emulsification, dispersion, and oil and water repellency. Based on these unique properties are numerous applications, some of which follow. Although applications are suggested for a particular use area, the general applicability of each concept is inferred for other applications.

PLASTICS AND RUBBER INDUSTRY

Emulsifying agent for polymerization, particularly fluoromonomers
As a latex stabilizer
To aid in the preparation of agglomerates of powdered fluorocarbon polymers.
In synergistic mixtures with hydrocarbon surfactants to wet low energy surfaces including natural and synthetic rubbers, resins, plastics
As an adjuvant for foam applications and as foaming agents to aid in leak detection.
As a foam additive to control spreading, crawling, edge build up.
As mould release agents, for silicones, etc.
In refractory processes
As an anti-mist film former
Additive for elimination of trapped air in plastic laminates
Wetting agent for resin molds for definition, strength
Hot-melt additive for oil and grease repellency
Resin additive for improved wetting of and bonding with fillers
Flow modifier for extruding hot melts: spreading, uniformity, anti-cratering
Adjuvant for resin etchant
Mold release agent, demoulding agent
Retarder for plasticizer migration or evaporation
Internal antistatic agent for polyolefins
Antiblocking agent for polyolefins

PETROLEUM INDUSTRY

Wetting assistant for oil well treatments, drilling muds
As a film evaporation inhibitor for gasoline, jet fuel, solvents, hydrocarbons
Lubricating, cutting oil improver, to improve penetration times
In extreme pressure EP lubricants
Oil spill collecting agent
Additive to improve tertiary oil well recovery

TEXTILE AND LEATHER INDUSTRY

Soil release and soil proofing agent
Oil/water repellent textile and leather treatment
Wetting agent to improve coverage and penetration of pores of substrates
Anti-foaming agent in textile treatment baths
Wetting agent for finish-on-yarn uniformity
Penetrating agent for finishes on tow, heavy denier fibers
Emulsifying agent/lubricant/ for fiber finishes Cleaner/metal treating agent for polymerization equipment
Flow modifer for spinning of hot melts, solutions
Additive for fabric finishes for spreading, uniformity
Wetting agent for dyeing
Penetration aid for bleaches
Wetting agent for binder in nonwoven fabrics

PAINT, PIGMENT AND FINISHING INDUSTRIES

Leveling, anti-cratering adjuvant for finishes and paints
Adjuvant for control of soiling
Agent to control differential evaporation of solvents
Leveling agent for floor waxes
Adjuvant for waxes to improve oil and water repellency
Adhesion improver for oily or greasy surfaces
To combat pigment flotation problems
Improver for automotive finishes, based on water-based coatings in which the pigments are rendered non-reactive
Pigment grinding aid to promote wetting, dispersion, color development
Foam generator substance for the appliction of dyes, inks
Electrolytic conversion coatings

MINING AND METALWORKING INDUSTRIES

In cleaning agents for property improvement
Additive for solvent cleaning
Additive for metal pickling baths to increase bath life and acid runoff
Additive for chrome electroplating: surface tension reduction, foaming
Additive for soldering flux, especially for electronic circuitry
Protective agent for coatings (tarnish resistance, grease repellency)
Corrosion inhibitor
Additive for etchant solution for improved definition
To form antimist films and anti-condensation surfaces
Plastic preplate and silicon etchant technology
In soldering flux for microelectronics to reduce foaming
In chemical roughing agent solutions, prior to galvanization
As a colloidal dispersion aid for magnetic solids
Protective coatings for aluminum and as an anti-blocking agent
Wetting agent for leaching copper ores and as a froth flotation agent
To promote ore wetting and quicker breaking of the protective oxide layer

PHARMACEUTICAL INDUSTRY

Improve the properties and penetration of antimicrobial agents
Improve the properties of biochemicals, biocides, algicides, bacteriocides, and bacteriostats
Improve the strength, homogeneity, and reduce the permeability of encapsulated materials
Emulsify fluorochemical blood substitutes

AGRICULTURE AND FORESTRY

Wetting agent for herbicides, fungicides, weed killers, hormone growth regulators, parasiticides, insecticides, germicides, bactericides, nematocides, microbiocides, defolients and fertilizers
As an ingredient in chemosterilents, insect repellents and toxicants
For wettable powder pesticides and chemical powders
Corrosion inhibitor for chemical applicators
Wetting agent for foliage
Wetting additive for live stock dips, or to wet sheep skins during desalination
Wetting adjuvant for manufacture of plywood veneer
Penetrant for preservative impregnation
Pulping aid
For cleaning tubes in paper making, dyeing
Grease/oil repellents for paper

FIRE FIGHTING

Wetting agent for fighting forest fires
Ingredient of AFFF, aqueous film forming extinguishing agents
Component of fluoroprotein foams
Additives to dry chemical extinguishing agents
Agent in aerosol-type extinguishers
Wetting agent for sprinkler water

AUTOMOTIVE, BUILDING MAINTENANCE AND CLEANING

Wetting agent for cleaning compositions
Additive for alkaline cleaners
Glass cleaner
Wetting agent for automobile waxes
Adjuvant to improve oil/water repellency of wax
Lubricant/corrosion inhibitor for antifreeze
Rinse-aid for car washes
In dry cleaning compositions and solvent cleaners, for water displacement and foaming. May improve soil suspension and decrease redespsition
Foaming agents for pipe cleaning
Anti-mist film foamer for glass and plastics
In foams for dust suppression
Cleaner for building exteriors
For acidic concrete cleaners
Air entrainment additive for low density concrete
Bubble foamer for air tracing, in ventilating system

HOUSEHOLD, COSMETIC AND PERSONAL PRODUCTS

Rinse-aid for dishwashing
Liquid polishing compositions
Floor polish leveling agent
Additive for alkaline oven cleaners
Synergistic improver for disinfectants
Carpet cleaners
Synergistic wetting agent in detergent formulations
Additive for protective coatings on metals (tarnish resistance, grease resistance)
Gloss and antistatic improver
Hair shampoo ingredient
Shaving foam ingredient
Oil and water repellent cosmetic powders ingredient
Ingredient of lotions or creams for skin or hair
Ingredient of skin protection creams

PHOTOGRAPHY AND GRAPHIC ARTS

Printing ink additive for ink flow and leveling, both aqueous and solvent based
Wetting agent for writing inks
To combat pigment flooding and floatation in printing inks
To form ink repellent surfaces for waterless lithoplates, or electrographic coatings.

Prevent reticulation of gelatin layers and improve uniformity
Assist in film drying
Improve film coatings and reduce "contraction flecks"

Wetting, leveling, anti-cratering assist agent
Surfactant for developer solutions
Photoemulsion stabilizer
Prevent photo-lubricant agglomeration
Coating aid in the preparation of multiple layer film elements
Antistatic wetting agent for film coatings
Antifogging agent for films
Bonding agent for fillers and fluoropolymer films
In coatings for neumatic liquid crystal cells The following examples are presented to illustrate the preparation of the novel compounds of this invention and to demonstrate their valuable surface active properties.

EXAMPLE 1

1,1-Dimethyl-10 (2-hydroxypropyl)amine 1-methyl-2(1,1,2,2-tetrahydro-perfluorooctanethio)propionimide $C_6F_{13}CH_2CH_2SCH_2CH(CH_3)CON^-N^+(CH_3)_2CH_2CHOHCH_3$ 1,1,2,2,-Tetrahydroperfluorooctanethiol (19.95 gms, 0.0525 moles), dimethyl (2-hydroxypropyl)amine methacrylimide (9.32 gms, 0.050 moles, and 2,2'azobis(methylpropionitrile) (0.093 gms) were reacted in acetonitrile (58.85 gms) at 70° C for 9 hours.

The product was stripped of volatiles at 70° C under moderate vacuum and then oiled out (the compound would not crystallize) of heptane and then hexane (3X) and dried (21.45 gms, 75.7% yield). On long-standing (1–2 months), the oil crystallized; m.p. 47°–57° C. An IR scan showed the disappearance of the unsaturation band at 1642 cm$^{-1}$.

Analysis for $C_{17}H_{23}F_{13}N_2O_2S$: Calc: C, 36.05; H, 4.09; F, 43.61; N, 4.95. Found: C, 36.52; H, 4.33; F, 42.52; N, 5.16.

EXAMPLE 2

1,1-Dimethyl-1-(2-hydroxypropyl)amine 1-methyl-2(1,1,2,2-tetrahydroperfluorodecanethio)propionimide

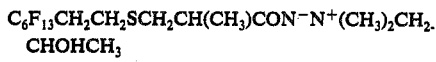

1,1,2,2-Tetrahydroperfluorodecanethiol (30.24 mgs, 0.063 moles), dimethyl(2-hydroxypropyl)amine methacrylamide (11.2 gms, 0.06 moles), and 2,2'-azobis(2-methylpropionitrile) (0.18 gm) were reacted in acetonitrile (83 gms) at 70° C for 10 hours. The product was stripped of all volatiles, dissolved in ether, filtered and dried. The product was washed 4 times with 500 ml heptane, recrystallized from heptane/benzene 95/5, and filtered. (19.3 gms, 48.3% yield) m.p. 71.4°–74° C. An IR scan showed the disappearance of the unsaturation band at 1642 cm$^{-1}$.

Analysis for $C_{19}H_{23}F_{17}N_2O_2S$: Calc: C, 34.24; H, 3.48; F, 48.46; N, 4.20. Found: C, 34.46; H, 3.40; F, 47.36; N, 4.42.

EXAMPLE 3

1,1-Dimethyl-1-(2-hydroxypropyl)amine 1-methyl-2(1,1,2,2-tetrahydroperfluorododecanethio)propionimide

1,1,2,2,-Tetrahydroperfluorododecanethiol (30.45 gms, 0.0525 moles), dimethyl(2-hydroxypropyl)amine methacrylimide (0.32 gms, 0.0500 moles), and 2,2'azobis (2-methylpropionitrile) (0.0932 gms) were reacted in acetonitrile (79.54 gms) at 75° C for 17 hours. 200 ml of additional acetonitrile was added and the product was dissolved, filtered, and crystallized (3 times from fresh solvent). It was then recrystallized from heptane 3 times and hexane 2 times. (16.65 gms, 43.5% yield) m.p. 83–85° C. A strong infrared absorption was found at 1581 cm$^{-1}$ (O$^-$C=N stretch). Purity was verified by TLC.

A thermogravimetric analysis at 5° C/min in nitrogen showed the sample to be weight-stable through its melt and up to about 135°–140° C. The initial stages of weight loss (140°–200° C) appeared to be vaporization, but at higher temperatures some decomposition was indicated by fluctuations in rate of weight loss NMR showed proton resonances at δ1.18, 6 protons, CH$\underline{CH_3}$×2; δ2.1–3.48, 10 protons, R$_f\underline{CH_2CH_2SCH_2}$CH + N$^+$-$\underline{CH_2}$ + $\underline{OH}$; δ3.51, 6 protons, N($\underline{CH_3}$)$_2$; δ4.37, 1 proton, $\underline{CHO}$.

These data are consistent for the structure of the product.

Analysis for $C_{21}H_{23}F_{21}N_2O_2S$: Calc: C, 32.91; H, 3.02; F, 52.05; N, 3.65. Found: C, 32.80; H, 2.82; F, 51.88; N, 3.46.

EXAMPLE 4

1,1-Dimethyl-1-(2-hydroxypropyl)amine 1-methyl-2(1,1,2,2,-tetrahydroperfluoroalkanethio)propionimide$^a$

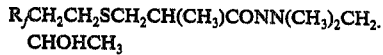

1,1,2,2-Tetrahydroperfluoroalkanethiol$^a$ (500 gms, 1.0 Mole), dimethyl (2-hydroxypropyl)amine methacrylimide (191 gms, 1.02 moles), and 2,2'-azobis(2-methylpropionitrile) (1.91 gms) were reacted in isopropanol (691 gms) with stirring, under nitrogen at 80° C for 1.7 hours. An IR scan showed the absence of acrylimide (no band at 1642 cm$^{-1}$) and the presence of a strong aminimide absorption at 1581 cm$^{-1}$.

$^a$The R$_f$ distribution is C$_6$, C$_8$, C$_{10}$ — 27:50 -23

The solvent was removed and all volatile impurities and starting reagents were removed at 10 microns Hg and 75° C. (627.3 gms, 92.8% yield). The original viscous product crystallized to a wax of m.p. 47°–51° C over a period of several days.

Analysis for R$_f\underline{CH_2Ch_2SCH_2}$C(CH$_3$)$_2$CH$_2$CHOHCH$_3$: Calc.: F, 47.0. Found: F, 47.3.
$^a$The R$_f$ distribution is C$_6$, C$_8$, C$_{10}$ — 27:50-23

EXAMPLE 5

Trimethylamine 1-methyl-2(1,1,2,2-tetrahydroperfluoroalkanethio)propionimide

1,1,2,2-Tetrahydroperfluoroalkanethiol[a] (250 gms, 0.5 moles), trimethylamine methacrylimide (71.1 gms, 0.5 moles), and 2,2'-azobis(2-methylpropionitrile) (0.71 gms) were reacted with stirring in isopropanol (322 gms) at 78° C for 2 hours.

An IR scan showed the absence of residual unsaturation at 1642 cm$^{-1}$ and the product was then stripped of volatiles under vacuum at 80° C to leave a viscous, clear fluid. Over a period of a week, the product crystallized to a wax m.p. 40°-48° C. NMR showed proton resonances at δ1.2, 3 protons, CH$\underline{CH}_3$; δ2.1-3.1, 7 protons R$_f\underline{CH}_2\underline{CH}_2$S$\underline{CH}_2\underline{CH}$; δ3.4, 9 protons, N(CH$_3$)$_3$.

These data are consistent for the structure of the product.

Analysis for R$_f$CH$_2$CH$_2$SCH$_2$CH(CH$_3$)CON$\bar{N}$(CH$_3$)$_3$ Calc.*: F, 50.55. Found: 50.57.

*Calculated from F-content of R$_f$ thior
[a]The R$_f$ distribution is C$_6$, C$_8$, C$_{10}$ — 27:50:23

EXAMPLE 6

1,1-Dimethyl-1-1(2-hydroxylpropyl)amine 5-(6)(1,1,2,2-tetrahydroperfluorodecanethio)norbornane 2-carboximide

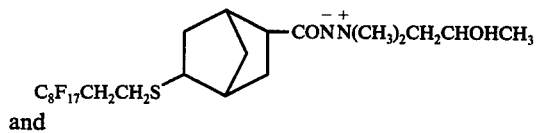

and

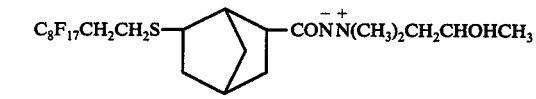

1,1,2,2-Tetrahydroperfluorodecanethiol (5.04, 0.0105 mole), 1,1-dimethyl-1-(2-hydroxypropyl)amine 5-norbornene-2-carboximide (2.38 g, 0.0100 mole, ethylene glycol dimethyl ether (7.42 g), and 2,2-azobis (2-methylpropionitrile) (0.04 g) were heated at 80° C for 2 hours. GLC showed complete consumption of theory) as a solid. NMR showed proton resonances at δ1.20, 3 protons, CHOH$\underline{CH}_3$; δ1.3 - δ3.4, 16 protons, (all other methylenes and methines); δ3.52, 6 protons, N$\underline{CH}_3$ × 2; δ4.32, 2 protons, $\underline{CHOH}$.

Analysis for C$_{23}$H$_{27}$F$_{17}$N$_2$O$_2$S: Calc.: C, 38.45; H, 3.78; F, 44.95; N, 3.90. Found: C, 37.98, H, 3.74; F, 44.03; N, 3.87.

EXAMPLE 7

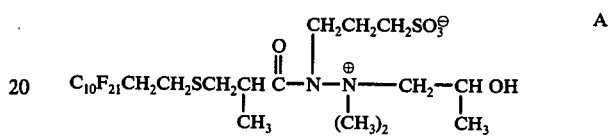 A

+

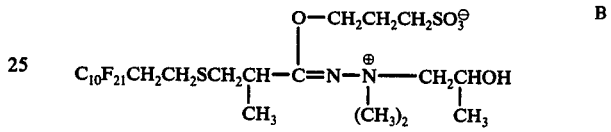 B (1,1,2,2-tetrahydroperfluorododecanethio)propionimide (3.45 g, 0.0045 mole), propane sultone (0.55 g, 0.0045 mole) and 4.0 g of glyme were refluxed for 14 hours in a flask which had been equipped with a thermometer, stirrer and a condenser protected with a drying tube. The product was only partially soluble in hot glyme. It was dissolved by adding 15 ml of Freon 113 to the mixture and warming. On subsequent cooling, the product precipitated as a tan powder (3.3 g) which was filtered and then recrystallized from a mixture of acetone and chloroform. The purified product (white powder, m.p. 75°-85° C) was obtained in a 63% yield (2.52 g). The NMR showed proton resonances at 1.3, 6 protons in overlapping doublets -CHC$\underline{H}_3$; 3.5, 6 protons in 2 sharp singlets, N—(CH$_3$)$_2$, the fact that the N-methyl signal occurs as 2 distinct but equal singlets suggests that the product is a 1:1 mixture of products A and B above: 4.3, one proton in an unresolved multiplet, CH$_2$C$\underline{H}$(CH$_3$)OH; 2.0-3.9, 16 protons in complex overlapping multiplets, R$_f\underline{CH}_2\underline{CH}_2$S$\underline{CH}_2$C$\underline{HH}_3$, N—C$\underline{H}_2$—, O$\underline{H}$, and a mixture of —O—$\underline{CH}_2\underline{CH}_2\underline{CH}_2$S and —N—$\underline{CH}_2\underline{CH}_2\underline{CH}_2$S.

These data are consistent with the structures

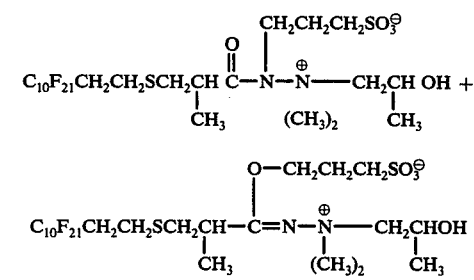

Analysis for C$_{24}$H$_{29}$F$_{21}$N$_2$O$_5$S$_2$: Calc.: C, 32.44; H, 3.29; F, 44.90; N, 3.15. Found: C, 30.90; H, 3.32; F, 43.91; N, 2.80.

EXAMPLES 8 and 9

Following the procedure of Example 1 the following compounds are prepared
(1) CF$_3$CH$_2$SCH$_2$C(CH$_3$)CONN̄(CH$_3$)$_3$
(2) C$_6$F$_{13}$CH$_2$CH$_2$SCH$_2$C(CH$_3$)CONN̄(CH$_3$)$_2$CH$_2$CH(OH)C$_8$H$_{17}$
by reacting respectively
(1) CF$_3$CH$_2$SH and CH$_2$ = C(CH$_3$)CONN̄(CH$_3$)$_3$
(2) C$_6$F$_{13}$CH$_2$CH$_2$SH and CH$_2$C(CH$_3$)CONN̄(CH$_3$)$_2$CH$_2$CH(OH)C$_8$H$_{17}$

EXAMPLE 10

Following the procedure of Example 7, the reaction product of Example 9 is reacted with 1,3-propane sultone to yield
(3) C$_6$F$_{13}$CH$_2$SCH$_2$C(CH$_3$)CON(CH$_2$CH$_2$CH$_2$SO$_3$)N$^+$(CH$_3$)$_2$CH$_2$CH(OH)C$_8$H$_{17}$ and C$_6$F$_{13}$CH$_2$CH$_2$SCH$_2$(CH$_3$COCH$_2$CH$_2$CH$_2$SO$_3^-$)=N(CH$_3$)$_2$CH$_2$CH(OH)C$_8$H$_{17}$ Table 1

| | Surface Properties of R$_f$-Aminimides | | | |
|---|---|---|---|---|
| | CONCENTRATION | | | |
| R$_f$-Aminimide | .1% | .01% | .001% | .0001% |
| Compound of Ex 1 | 18.0 | 17.9 | 31.4 | 55.8 |
| Compound of Ex 2 | 16.0 | 16.9 | 19.9 | 66.5 |
| Compound of Ex 3 | | | insoluble | |
| Compound of Ex 4 | 18.7 | 18.9 | 29.3 | 52.0 |
| Compound of Ex 5 | 17.3 | 18.7 | 34.8 | 68.5 |
| Compound of Ex 6 | 19.6 | 18.7 | 44.7 | 60.0 |

What is claimed is:
1. A perfluoroalkylthioaminimide of the formula

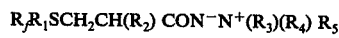

wherein $R_f$ is straight or branched chain perfluoroalkyl of 1 to 18 carbon atoms or said perfluoroalkyl substituted by perfluoroalkoxy of 2 to 6 atoms;

$R_1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms;

$R_2$ is hydrogen or straight or branched chain alkyl of 1 to 6 carbon atoms;

$R_3$ and $R_4$ each is independently straight or branched chain alkyl of 1 to 22 carbon atoms and $R_5$ is straight or branched chain alkyl of 1 to 22 carbon atoms that may also contain 1 or 2 hydroxyl groups.

2. A compound of claim 1 wherein $R_f$ has 6 to 12 carbon atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen or methyl as a third substituent;

$R_2$ is hydrogen or methyl;

$R_3$ and $R_4$ have independently 1 to 12 carbon atoms, and $R_5$ is straight chain alkyl of 1 to 3 carbon atoms that may also contain 1 hydroxyl group.

3. The compound of claim 1 which is 1,1-Dimethyl-1-(2-hydroxypropyl)amine 1-methyl-2(1,1,2,2-tetrahydroperfluorooctanethio)propionimide.

4. The compound of claim 1 which is 1,1-Dimethyl-1-(2-hydroxypropyl)amine 1-methyl-2(1,1,2,2-tetrahydroperfluorodecanethio)pripionimide.

5. The compound of claim 1 which is 1,1-Dimethyl-1-(2-hydroxypropyl)amine 1-methyl-2(1,1,2,2-tetrahydroperfluorododecanethio)propionimide.

6. The compound of claim 1 which is 1,1-Dimethyl-1-(2-hydroxypropyl)amine 1-methyl-2(1,1,2,2-tetrahydroperfluoroalkanethio)propionimide.

7. The compound of claim 1 which is Trimethylamine 1-methyl-2-(1,1,2,2-tetrahydroperfluoroalkanethio)propionimide.

8. 1,1-Dimethyl-1-1(2-hydroxypropyl)amine 5-(6) (1,1,2,2-tetrahydroperfluorodecanethio)norbornane 2-carboximide.

* * * * *